(12) United States Patent
Kobayashi et al.

(10) Patent No.: US 7,442,553 B2
(45) Date of Patent: Oct. 28, 2008

(54) METHOD FOR DETERMINING THE AMOUNT OF THE MALEIMIDYL GROUPS OF A PARTICLE

(75) Inventors: Takako Kobayashi, Minamiashigara (JP); Hiroshi Yamamoto, Minamiashigara (JP); Chisato Urano, Minamiashigara (JP); Yoshihiro Inaba, Minamiashigara (JP)

(73) Assignee: Fuji Xerox Co., Ltd., Tokyo (JP)

( * ) Notice: Subject to any disclaimer, the term of this patent is extended or adjusted under 35 U.S.C. 154(b) by 824 days.

(21) Appl. No.: 11/052,923

(22) Filed: Feb. 9, 2005

(65) Prior Publication Data

US 2006/0051871 A1    Mar. 9, 2006

(30) Foreign Application Priority Data

Sep. 6, 2004    (JP)    ............................ 2004-259068

(51) Int. Cl.
  *G01N 33/44*    (2006.01)
  *G01N 33/545*    (2006.01)

(52) U.S. Cl. .................. 436/85; 436/106; 436/127; 436/172; 436/528; 436/531; 436/534

(58) Field of Classification Search .................. 436/85, 436/106, 127, 172, 183, 528, 531, 534
See application file for complete search history.

(56) References Cited

U.S. PATENT DOCUMENTS

| | | | | |
|---|---|---|---|---|
| 3,857,931 A | * | 12/1974 | Hager | ......................... 436/509 |
| 3,891,669 A | * | 6/1975 | Kanaoka et al. | ............. 548/525 |
| 4,268,663 A | * | 5/1981 | Skold | ......................... 536/17.8 |
| 4,847,209 A | * | 7/1989 | Lewis et al. | .................. 436/533 |
| 4,968,742 A | * | 11/1990 | Lewis et al. | ................. 525/54.1 |
| 4,988,625 A | * | 1/1991 | Marburg et al. | ................ 436/5 |
| 5,132,226 A | * | 7/1992 | Dreher et al. | .................. 436/86 |
| 5,169,754 A | * | 12/1992 | Siiman et al. | ................... 435/5 |
| 5,525,524 A | * | 6/1996 | Buechler et al. | ............ 436/518 |
| 5,576,216 A | * | 11/1996 | Patchornik | ..................... 436/86 |
| 5,639,620 A | * | 6/1997 | Siiman et al. | .............. 435/7.21 |
| 7,094,860 B2 | * | 8/2006 | Inaba et al. | .................. 528/191 |
| 2004/0039109 A1 | * | 2/2004 | Urano et al. | ................. 524/548 |

FOREIGN PATENT DOCUMENTS

| | | | |
|---|---|---|---|
| JP | 5-107249 A | 4/1993 |
| JP | 7-265096 A | 10/1995 |
| JP | 9-252799 A | 9/1997 |

OTHER PUBLICATIONS

Palit, S. R. et al, Journal of Polymer Science 1962, 58, 1225-1232.*

(Continued)

*Primary Examiner*—Arlen Soderquist
(74) *Attorney, Agent, or Firm*—Sughrue Mion, PLLC

(57) ABSTRACT

A method for quantitatively determining the amount of maleimidyl groups on a polymer fine particle containing at least maleimidyl groups, by allowing a fluorescent material having an SH group to react with the maleimidyl groups and determining the amount of maleimidyl groups by means of measuring the fluorescence of the fluorescent material.

13 Claims, 1 Drawing Sheet

OTHER PUBLICATIONS

Huffman, K. R. et al, Journal of Polymer Science, Polymer Chemistry Edition 1985, 23, 1939-1954.*

Jayasuriya, R. M. et al, Journal of Polymer Science, Polymer Chemistry Edition 1985, 23, 2819-2832.*

Yan, C. et al, Journal of Applied Polymer Science 1990, 40, 89-98.*

Shmanai, V. V. et al, Vestsi Akademii Navuk Belarusi, Seryya Khimichnykh Navuk 1995, 9-13.*

Scoble, J. A. et al, Journal of Chromatography, A 1996, 752, 67-76.*

Nashat, A. H. et al, Biotechnology and Bioengineering 1998, 60, 137-146.*

Thomas, I. P. et al, Chemical Communications 1999, 1507-1508.*

Alvarez-Blanco, S. et al, Polymer Bulletin 2001, 47, 329-336.*

* cited by examiner

METHOD FOR DETERMINING THE AMOUNT OF THE MALEIMIDYL GROUPS OF A PARTICLE

CROSS REFERENCE TO RELATED APPLICATIONS

This application claims priority under 35USC 119 from Japanese Patent Application No. 2004-259068, the disclosure of which is incorporated herein by reference.

BACKGROUND OF THE PRESENT INVENTION

1. Field of the Invention

The present invention relates to a method of quantitatively determining the amount of functional groups of a polymer particle having functional groups that can be used favorably in applications such as a carrier for diagnostic and pharmaceutical products, a carrier for chromatography, a viscosity adjuster, a resin molding material, a paint additive, a crosslinking/hardening agent, and a cosmetic additive, and in particular to a method of quantitatively determining the amount of functional groups of a polymer particle having maleimidyl groups as the functional groups.

2. Description of the Related Art

Polymer particles having a particle diameter in the range of approximately 0.01 to 100 µm have been used favorably in such applications as a carrier for diagnostic and pharmaceutical products, a carrier for chromatography, a carrier for combinatorial chemistry, a viscosity adjuster, a resin molding material, a paint additive, a crosslinking/hardening agent, and a cosmetic additive, and it is important to determine the amount of functional groups quantitatively for control of the properties of the particles.

Conventional quantitative methods of determining the amount of functional groups of a polymer particle include, for example, a method of determining the acid value and the hydroxyl value of a polymer as specified in Japanese Industrial Standard (JIS) K0070 and a method of determining the amount of amino groups of a plastic material as specified in JIS K7245. These methods, which are intended for use in analysis of general polymeric materials, need a large amount of a sample, a long period of time, and many steps of procedures for analysis. In addition, Journal Soc. Syn. Org. Chem. Vol. 60, No. 5, pp. 454 to 463 discloses analysis of the absorption peaks obtained by infrared spectroscopic analysis of a particle surface and ultraviolet and visible light analysis that determines the degree of reaction between a particle and a reagent by comparison with that determined in a blank test as methods for determining the amount of functional groups of a particle. In these analytical methods which do not determine the amount of functional groups directly, the particles having the same amount of functional groups often differ in actual properties and the values obtained often vary significantly depending on the surface state of the samples.

A method of determining the amount of maleimidyl groups is disclosed in the General Catalog of Dojindo Laboratories, 23rd Ed., pp. 80 and 81. The method, which is intended for use in analysis of general compounds, needs a large amount of a sample, a long period of time, and many steps of procedures for analysis, similar to the methods of determining functional groups above.

On the other hand, a flow cytometer is an instrument that analyzes the fluorescence intensity, the scattering intensity, and the number of particles; and methods utilizing a flow cytometer include, for example, a method of measuring the coagulative state of latex particles described in Japanese Patent Application Laid-Open (JP-A) No. 5-107249, a quantitative method of determining the amount of a cyst of algae descried in JP-A No. 7-265096, and a quantitative method of determining the amount of phosphorus-accumulating microbes in sludge described in JP-A No. 9-252799. These methods, each of which compares the fluorescence intensity of particles qualitatively, mainly focus on counting the number of particles in analysis and thus cannot be applied to quantitative analysis of the amount of the functional groups of particles.

SUMMARY OF THE INVENTION

The present invention has been made in view of the above circumstances and provides a first aspect of the present invention which is a method for quantitatively determining the amount of maleimidyl groups of a polymer particle containing at least maleimidyl groups, the method comprising allowing a fluorescent material having an SH group to react with the maleimidyl groups and measuring the fluorescence of the fluorescent material.

DETAILED DESCRIPTION OF THE INVENTION

Figure 1:
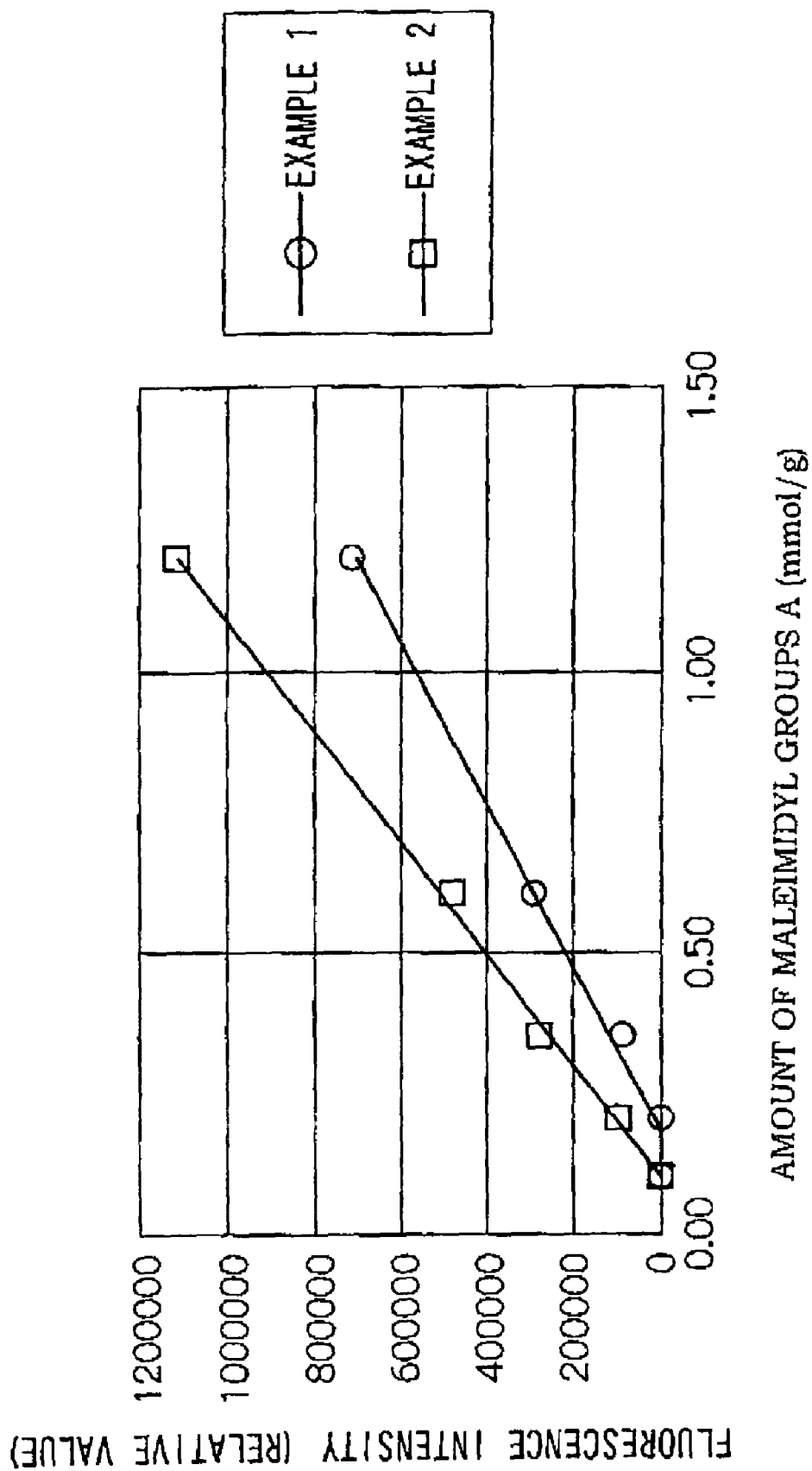
FIG. 1 is a chart illustrating the results obtained in Examples 1 and 2.

The present invention relates to a method for determining the amount of maleimidyl groups of a particle by allowing a fluorescent material having an SH group to react with the maleimidyl groups of a polymer particle containing at least maleimidyl groups and measuring the amount of the fluorescence emitted from the particle.

The invention also relates to a method for determining the amount of maleimidyl groups of a particle by using a flow cytometer for measurement of the amount of the fluorescence emitted from the particle.

The invention further relates to a method for determining the amount of maleimidyl groups of a particle by allowing a fluorescent material to react with a polymer particle at a molar ratio of the fluorescent material to the total amount of maleimidyl groups of the polymer particle of approximately 1:1 to 1:100.

Hereinafter, the invention will be described in detail.

1. Fluorescent Material having an SH Group

The fluorescent material for use in the invention can react with the maleimidyl groups present on a particle. It is a compound having an SH group in the structure of the fluorescent material, and more specifically, a fluorescent material prepared by bonding a fluorescent dye to a compound having an SH group (thiol compound). The fluorescent material can be prepared, for example, by allowing the functional groups of a fluorescent dye having isothiocyanic acid groups, dichlorotriazine groups, succinimide groups, carboxyl groups, or the like to react with the hydroxyl, amino, or other group of a thiol compound; but the method of preparation is not limited thereto as long as the two compounds can be bonded to each other.

Typical examples of the fluorescent dyes include fluorescein thioisocyate, dichlorotriazylaminofluorescein, carboxyfluorescein succinimidylether, carboxyfluorescein, and the like; 5-DTAF, FITC, FAM, SFX, and others provided from Molecular Probes; and compounds such as 9-anthroylnitrile and dansylaminophenylboric acid, which do not contain the functional group described above but are still reactive with the functional groups of the particle, but the invention is not limited thereto. A preferably fluorescent dye is a mercaptoalkylfluorescein dye such as mercaptoethylfluorescein or mercaptopropylfluorescein, and more preferable mercaptoethylfluorescein.

Examples of the thiol compounds include cysteine, cysteamine, aminoethanethiol, mercaptoamine, glutathione, mercaptoethanol, DTT, DTE, peptide compounds containing cysteine as the constituent amino acid, and the like, but the invention is not limited thereto. In addition, even dimers of these compounds may be used after reaction with a fluorescent dye and reduction with a reducing agent to form SH groups. Preferable examples of the thiol compounds include cysteine, aminoethanethiol, mercaptoamine, glutathione, mercaptoethanol, DTT, and DTE, and more preferable examples thereof include cysteine, aminoethanethiol, mercaptoamine, and glutathione.

The reaction ratio of the fluorescent dye to the thiol compound is in the range of approximately 1:1 to 1:10 (the fluorescent dye:the thiol compound) and preferably in the range of approximately 1:1 to 1:5. The reaction conditions of the fluorescent dye and the thiol compound for preparing the fluorescent material are not particularly limited. For example, a method of dispersing a certain amount of a thiol compound in fluorescent dye solution and allowing the mixture to react for a certain period of time may be used. The mixture may or may not be heated at that time. Since the thiol compound is vulnerable to oxidation resulting in conversion of the SH groups to S—S bonds, the SH groups may be formed in the presence of a reducing agent such as aminoethanethiol, mercaptoamine, DTE, or the like as needed after the reaction of the fluorescent dye and the thiol compound. The fluorescent material thus obtained may be purified as needed by for example chromatography.

In the quantitative determination according to the invention, favorable examples of the fluorescent materials having an SH group include mercaptoethylfluorescein, mercaptopropylfluorescein, and compounds obtained in the reaction of FITC and an amino acid or a peptide having one or more SH groups, and more preferable examples include mercaptoethylfluorescein and the compound obtained by the reaction of FITC and glutathione.

2. Polymer Particles Containing Maleimidyl Groups

The polymer particles containing maleimidyl groups according to the invention are those having maleimidyl groups on the surface of or in the particles, and examples of methods of preparation thereof include methods of preparing particles by suspension-polymerization of a monomer having a maleimidyl group in a medium, and of introducing maleimidyl groups onto a base particle for the polymer particle. However, the method of preparation is not limited thereto.

Examples of the base particles for polymer particle are polymer particles having a (meth)acrylate polymer, and typical examples thereof include polymer particles of the polymers such as t-butyl(meth)acrylate, 2-methyl-2-butyl(meth)acrylate, benzyl(meth)acrylate, methoxybenzyl(meth)acrylate, ethoxybenzyl(meth)acrylate, dimethoxybenzyl(meth)acrylate, methylbenzyl(meth)acrylate, dimethylbenzyl(meth)acrylate, ethylbenzyl(meth)acrylate, and 4-fluorobenzyl(meth)acrylate, and the like. Among them, polymers from a monomer such as t-butyl(meth)acrylate or benzyl(meth)acrylate are particularly preferable from the viewpoints of the availability, price, and reactivity of monomer.

A homopolymer from a single monomer or a copolymer with other monomer(s) may be used for the polymer particle. Any known process may be used for preparing the particle. Favorable examples thereof include suspension polymerization process, emulsion polymerization process, dispersion polymerization process, and seeding polymerization process. In addition, the suspension polymerization may be carried out by the emulsification process known as membrane emulsification process.

The particle may be a crosslinked polymer particle prepared in the presence of a cross-linking agent as needed. In such a case, the crosslinking method is not particularly limited, and the particle may be crosslinked during or after polymerization. The crosslinking may be carried out, for example, by addition of a cross-linking agent, irradiation of an electromagnetic wave, irradiation of an electron beam, or irradiation of a particle beam. The cross-linking agent is not particularly limited, and examples thereof include divinylbenzene, urea resins, melamine resins, and the like.

Methods of introducing maleimidyl groups into the particle include various known a method but are not limited thereto.

Examples thereof include (1) polycondensation of a polymer particle containing hydroxyl groups and hydroxymethyl maleimide in the presence of an esterification catalyst; (2) method of introducing maleimidyl groups to a polymer particle containing amino groups with a bifunctional reagent such as N-(6-maleimidocaproyloxy)succinimide; (3) method of preparing a polymer particle having ester-exchangeable functional groups such as t-butyl(meth)acrylate polymer and allowing the polymer to react with a maleimide compound having a hydroxyl group such as hydroxymethyl maleimide in the presence of an ester-exchange catalyst such as tetra-n-propoxytitanium in an ester-exchange reaction; (4) method of preparing a polymer particle having carboxylic acid groups and allowing the polymer to react with a maleimide compound having a hydroxyl group such as hydroxymethyl maleimide in a dehydration reaction; and the like.

Methods of introducing maleimidyl groups into a hydroxyl group-containing polymer include a method of previously preparing particles by suspension polymerization of a monomer having a functional group that can be converted to a hydroxyl group in an aqueous medium and converting the functional groups of the polymer to hydroxyl groups; a method of previously preparing polymer particles having reactive functional groups and introducing hydroxyl groups to the particles by allowing the reactive functional groups of the particles to bond to a hydroxyl group-containing compound; and a method of previously preparing a polymer having ester-exchangeable functional groups such as a t-butyl(meth)acrylate polymer and introducing hydroxyl groups thereto by allowing a diol such as ethylene glycol to react with the functional groups in the presence of an ester-exchange catalyst such as tetra-n-propoxytitanium.

Methods of preparing the amino group-containing polymer particles include a method of previously preparing polymer particles having reactive functional groups and introducing amino groups by allowing an amino group-containing compound to react with the reactive functional groups of the particles; and a method of preparing polymer particles having ester-exchangeable functional groups such as t-butyl(meth)acrylate polymer and allowing a diamine such as 1,6-diaminohexane to react with the amino groups of the particles in the presence of an ester-exchange catalyst such as tetra-n-propoxytitanium.

The bond between the polymer particle and the maleimidyl group may be any one of bonds including an ether bond, an ester bond, an amide bond, and the like.

In addition, the polymer particle according to the invention may contain any functional groups other than the maleimidyl groups. The functional groups other than the maleimidyl group are not particularly limited, but include, for example, hydroxyl and amino groups, precursor residues thereof, as well as other functional groups that do not inhibit the reaction of the maleimidyl groups including sulfonate groups, nitro groups, alkyl groups, and benzyl groups.

The size of the polymer particle having maleimidyl groups according to the invention is in the range of approximately 0.5 μm to 100 μm, preferably in the range of approximately 1 μm to 50 μm, as a particle diameter. A particle smaller than the range above is not favorable as it becomes more difficult to detect the particle in a flow cytometer. A particle larger than the range above is also not favorable, as the particle cannot pass through the detection nozzle of the flow cytometer.

3. Quantitative Determination Method

First, a fluorescent material is bound to the maleimidyl groups of a polymer particle by allowing the fluorescent material to react with the maleimidyl groups of polymer particle.

The molar ratio of the maleimidyl groups on particle to the fluorescent material supplied during reaction is preferably in the range of approximately 1:1 to 100:1 (the maleimidyl groups:the fluorescent material) and more preferably in the range of approximately 2:1 to 20:1. Generally in instrumental analysis, the amount of dye that reacts with functional groups is usually prepared one to several times more than (by molar ratio) that of the functional groups. In the invention, addition of the fluorescent material in a molar ratio larger by one time than the amount of the maleimidyl groups of particle is disadvantageous, because the dye precipitates in the reaction solution due to saturation or the fluorescent dye is incorporated into the particle excessively. Alternatively, an amount of maleimidyl groups smaller than a molar ratio of approximately 1/100 with respect to the fluorescent material is unfavorable, because the smaller amount of fluorescent dye present leads to fluorescence not sufficient for quantitative determination of the particle.

Although the mechanism of the quantitative determination of the invention is yet to be clearly understood, the fluorescent material does not react with 100% of the maleimidyl groups of the particle, but rather the fluorescent material reacts with the maleimidyl groups at a certain rate based on the molar ratio of the fluorescent material. And then the particle having the maleimidyl groups dyes, and thus the quantitative determination of the amount of the maleimidyl groups of particle appears to be possible by measuring the intensity of fluorescence. It is revealed that the speed of the reaction of maleimidyl groups with the fluorescent material varies according to the substrate used for the particle carrier to which the maleimidyl groups are bonded, but that the reaction ratio does not. Accordingly, even if the kinds of polymer particle having the maleimidyl groups vary, it is possible to determine quantitatively the amount of the maleimidy groups by preparing a certain amount of the fluorescent material.

The reaction condition between the particle and the fluorescent material is not particularly limited; and, for example, a method of dispersing a certain amount of particles in a solution of a fluorescent material and allowing the mixture to react for a certain period of time while mixed may be used because the reaction between the maleimidyl group and SH group proceeds under a mild condition; but the invention is not limited to this method.

As an example of the method for quantitative determination of the amount of the maleimidyl groups of a particle, it is possible to adopt a method of dying particles having a known amount of maleimidyl groups and a particle having an unknown amount of maleimidyl groups separately under the same conditions, measuring the fluorescence of the particles by a flow cytometer, preparing a calibration curve from the amounts of maleimidyl groups of the known samples and the fluorescence intensities, and thereby determining the amount of maleimidyl groups in the unknown sample.

Any common method may be used for the measurement of fluorescence by a flow cytometer. Before measurement, maleimidyl group-containing polymer particles previously modified with a fluorescent material are first dispersed in a sheath fluid for a flow cytometer. It is possible to determine fluorescence by measuring the dispersion directly by a flow cytometer.

The amount of sample required for measurement in a flow cytometer is approximately 1 to 10 mg, which is extremely smaller than the amount required for conventional quantitative determination methods. In addition, use of a flow cytometer allows direct determination of the maleimidyl group-containing particles to which the fluorescent material is bound, eliminating the tedious operations required for conventional two-dimensional quantitative methods.

Hereinafter, the invention will be described in detail with reference to Examples. It should be understood that the invention is not restricted to these Examples. "Part" in the following Examples means "part by weight".

EXAMPLES (Preparation of Crosslinked Polymer Particles Containing Hydroxyl Groups)

100 parts of t-butyl methacrylate (manufactured by Wako Pure Chemical Industries) and 5 parts of divinylbenzene (purity 55%) are polymerized by suspension polymerization, and the resulting polymer particles are classified, to give crosslinked polymer particles having an average particle diameter of 15 μm. The particles obtained are washed with ion-exchange water and a solvent, separated, and dried, to give crosslinked polymer fine particles. 10 parts of the crosslinked polymer particles obtained are dispersed in 50 parts of polyethylene glycol 200 (manufactured by Wako Pure Chemical Industries); 15 parts of mesitylene (manufactured by Wako Pure Chemical Industries) is added to the mixture. And further, 0.2 part of tetra-n-propoxy titanium is added dropwise in a nitrogen atmosphere; and the mixture is allowed to react under reflux for 3, 5, 7, 10, or 14 hours. The particles thus obtained are respectively redispersed and washed in methanol, and then washed with ion-exchange water and a solvent, separated and dried, to give hydroxyl group-containing crosslinked polymer particles 1 to 5.

(Preparation of Hydroxymethyl Maleimide)

A mixture of 24 parts of maleimide (manufactured by Aldrich), 21 parts of an aqueous 35 wt % formaldehyde solution (manufactured by Wako Pure Chemical Industries), and 0.7 part of an aqueous 5 wt % sodium hydroxide solution is allow to react at 40° C. for 2 hours, to give white crystalline hydroxymethyl maleimide. The crystals are filtered under reduced pressure and dried under reduced pressure at room temperature. The crude crystalline hydroxymethyl maleimide is recrystallized in ethyl acetate, to give 22 parts of hydroxymethyl maleimide.

(Preparation of Crosslinked Polymer Particles Containing Maleimidyl Groups)

17 parts of the hydroxymethyl maleimide thus prepared and 500 parts of toluene are added to 10 parts of the maleimidyl group-containing crosslinked polymer particles 1 to 5. Each of the mixtures is stirred under heat at 60 to 70° C., and added 0.4 part of p-toluenesulfonic acid monohydrate as a catalyst. And then each of the mixtures is heated and allowed to react under reflux additionally for 10 hours. The particles obtained are then dispersed and washed in methanol, washed again with ion-exchange water and a solvent, and further, redispersed and washed in a phosphate buffer at pH 7 containing 2NA (manufactured by Dojindo Laboratories) and sodium chloride (manufactured by Wako Pure Chemical Industries), washed with ion-exchange water, and separated and dried, to give maleimidyl group-containing crosslinked polymer particles.

(Preparation of a Fluorescent Material)

0.09 Part of glutathione reduced form (manufactured by Wako Pure Chemical Industries) and 0.25 part of FITC-I (manufactured by Dojindo Laboratories) are dissolved in 1,000 parts of a phosphate-buffered physiological saline (PBS) (manufactured by Wako Pure Chemical Industries), and the mixture was stirred at room temperature for 1 hour. The reaction product is separated and purified by chromatography by using PBS as the running buffer, to give 10 parts of reaction solution A containing the fluorescent material. The amount of SH groups in the reaction solution thus obtained is $2.5 \times 10^{-5}$ mol/L as determined by using DTNB (manufactured by Dojindo Laboratories).

(Determination of Fluorescence Intensity)

| | |
|---|---|
| Maleimidyl group-containing crosslinked polymer particle; | 0.002 part |
| Reaction solution A; | 1 part |

The composition above is placed in a capped test tube and stirred in a shaker at room temperature for 2 hours. The sample in the capped test tube is centrifuged at 3,000 rpm for 5 minutes, making the mixture separate into particles and supernatant liquid, and the particles are washed repeatedly by ultrasonic redispersion of the particles in PBS (manufactured by Wako Pure Chemical Industries) and centrifugation.

The particles are dispersed in a sheath fluid for a flow cytometer (FACS FLOW manufactured by Beckton & Dickinson) and the fluorescence intensity thereof is determined by using a flow cytometer (Facs Calibur, manufactured by Beckton & Dickinson) under the same measuring conditions at a detection wavelength of 530 nm.

(Determination of the Amount of Maleimidyl Groups by Using a Spectrophotometer)

| | |
|---|---|
| 2-Mercaptoethylamine hydrochloride salt; | 0.05 part |
| PBS (manufactured by Wako Pure Chemical Industries); | 98.45 parts |

-continued

| | |
|---|---|
| EDTA 2Na, dihydrate (2NA) (manufactured by Dojindo Laboratories); | 1.5 parts |

A solution having the composition above is prepared and designated reaction solution B.

| | |
|---|---|
| Maleimidyl group-containing crosslinked polymer particle; | 0.01 part |
| Reaction solution B; | 10 parts |

The composition above is placed in a capped test tube, stirred, and centrifuged for 5 minutes for removal of the particles, to give reaction solution C.

| | |
|---|---|
| Reaction solution C; | 0.2 part |
| Aqueous 0.1 mol/L hydrogen disodium phosphate dodecahydrate (manufactured by Wako Pure Chemical Industries) solution; | 1 part |
| 5 mmol/L DTNB (manufactured by Dojindo Laboratories) ethanol solution; | 0.5 part |
| Ultrapure water; | 23.3 parts |

The amount of 2-mercaptoethylamine B (mol) in the supernatant liquid solution is determined by the molar extinction coefficient $\epsilon$ of 16,800 calculated by the absorbance at 412 nm with a spectrophotometer (U-4000, manufactured by Hitachi Ltd.). The amount of 2-mercaptoethylamine C (mol) in the system not containing the sample is also determined as the blank value and the amount of maleimidyl groups A (mmol/g) is calculated according to the following equation:

$$A = (C-B)/w \times 1,000$$

wherein, w represents the weight of the particles (g).

Example 2

| | |
|---|---|
| Maleimidyl group-containing crosslinked polymer particle; | 0.00025 part |
| Reaction solution A; | 1 part |

A particle is prepared in a similar manner to Example 1 except that the amount of the maleimidyl group-containing crosslinked polymer particle is altered.

<Result>

Measurement results in Examples 1 and 2 are summarized in Table 1 and the graph obtained from the data is shown in FIG. 1. In addition, the estimated molar ratio supplied at the start of reaction of the fluorescent material to the amount of hydroxyl groups on the particle calculated from the amount of maleimidyl groups A (mmol/g) is also included in Table 1. In FIG. 1, the abscissa axis represents the amount of maleimidyl groups as determined in Comparative Example, while the ordinate axis represents the relative value of the fluorescence determined by a flow cytometer.

TABLE 1

| | Example 1 | | Example 2 | |
| --- | --- | --- | --- | --- |
| | Fluorescence intensity (relative value) | Estimated molar ratio (fluorescent material:maleimidyl group supplied) | Fluorescence intensity (relative value) | Estimated molar ratio (fluorescent material:maleimidyl group supplied) |
| Maleimidyl group-containing crosslinked polymer particle 1 | 1200 | 1:8.0 | 2377 | 1:1.0 |
| Maleimidyl group-containing crosslinked polymer particle 2 | 3612 | 1:16.0 | 97157 | 1:2.0 |
| Maleimidyl group-containing crosslinked polymer particle 3 | 89630 | 1:28.0 | 280944 | 1:3.5 |
| Maleimidyl group-containing crosslinked polymer particle 4 | 28900 | 1:48.0 | 483228 | 1:6.0 |
| Maleimidyl group-containing crosslinked polymer particle 5 | 715800 | 1:96.0 | 1117028 | 1:12.0 |

As apparent from FIG. 1, the measurement methods of Examples 1 and 2 provide a linear relationship between the amount of the maleimidyl groups on particle and the fluorescence intensity. The result clearly indicates that it is possible to determine quantitatively the fluorescence intensity of the particles of Examples 1 and 2 according to the amount of maleimidyl groups as determined by a measuring method of Comparative Example.

Example 3

Maleimidyl group-containing crosslinked polymer particles are prepared in a similar manner to the method described in Example 1, except that the newly prepared following hydroxyl group-containing crosslinked polymer particles 10 to 15 are used, and the fluorescence intensities of these particles are determined in a similar manner to Example 1.

(Preparation of Hydroxyl Group-Containing Crosslinked Polymer Particles 10 to 15)

Hydroxyl group-containing crosslinked polymer particles 10 to 15 are obtained in a similar manner to Example 1, except that 100 parts of t-butyl methacrylate (manufactured by Wako Pure Chemical Industries) is replaced with 57.7 parts of t-butyl methacrylate (manufactured by Wako Pure Chemical Industries) and 42.3 parts of styrene (manufactured by Wako Pure Chemical Industries).

(Result)

Determination of the fluorescence intensity of the maleimidyl group-containing crosslinked polymer particles prepared from the hydroxyl group-containing crosslinked polymer particles 10 to 15 in a method similar to Example 1 reveals that the polymers also provide a linear relationship between the amount of maleimidyl groups and the fluorescence intensity. The result clearly indicates that the method according to the invention allows quantitative determination even if the composition of the crosslinked polymer particle is changed.

What is claimed is:

1. A method for quantitatively determining the amount of maleimidyl groups of a polymer particle containing at least maleimidyl groups, the method comprising allowing a fluorescent material having an SH group to react with the maleimidyl groups and measuring the fluorescence of the fluorescent material.

2. The quantitative determination method according to claim 1, wherein said fluorescence is determined by a flow cytometer.

3. The quantitative determination method according to claim 2, comprising allowing said fluorescent material to react with said polymer particle at a molar ratio of said fluorescent material to the total amount of maleimidyl groups of the polymer particle of approximately 1:1 to 1:100.

4. The quantitative determination method according to claim 2, wherein said fluorescent material is prepared by binding a fluorescent dye to a thiol compound having an SH group.

5. The quantitative determination method according to claim 4, wherein the fluorescent dye has at least one functional group selected from the group consisting of an isothiocyanic acid group, a dichlorotriazine group, a succinimide group, and a carboxyl group.

6. The quantitative determination method according to claim 4, wherein said fluorescent dye is a mercaptoalkylfluorescein.

7. The quantitative determination method according to claim 4, wherein said thiol compound has a hydroxyl group and/or an amino group.

8. The quantitative determination method according to claim 4, wherein the thiol compound is at least one compound selected from the group consisting of cysteine, aminoethanethiol, mercaptoamine, and glutathione.

9. The quantitative determination method according to claim 4, wherein the fluorescent material is prepared by reacting the fluorescent dye with the thiol compound having an SH group at a ratio of approximately 1:1 to 1:10.

10. The quantitative determination method according to claim 4, wherein the fluorescent material is prepared by reacting the fluorescent dye with the thiol compound having an SH group at a ratio of approximately 1:1 to 1:5.

11. The quantitative determination method according to claim 2, comprising allowing said fluorescent material to react with the polymer particle at a molar ratio of the fluorescent material to the total amount of maleimidyl groups of the polymer particle of approximately 1:2 to 1:20.

12. The quantitative determination method according to claim 2, wherein the particle diameter of said polymer particle is approximately 0.5 to 100 µm.

13. The quantitative determination method according to claim 2, wherein the particle diameter of said polymer particle is approximately 1 to 50 µm.

* * * * *